(12) United States Patent
Orlewicz et al.

(10) Patent No.: US 7,096,869 B1
(45) Date of Patent: Aug. 29, 2006

(54) DEVICE AND METHOD FOR MAINTAINING AN AIRWAY

(76) Inventors: Marc S. Orlewicz, 1656 Lexington, Plymouth, MI (US) 48170; Dennis J. Orlewica, 1656 Lexington, Plymouth, MI (US) 48170

( * ) Notice: Subject to any disclaimer, the term of this patent is extended or adjusted under 35 U.S.C. 154(b) by 109 days.

(21) Appl. No.: 11/093,774

(22) Filed: Mar. 30, 2005

(51) Int. Cl.
*A61G 15/00* (2006.01)
(52) U.S. Cl. .................................... 128/845
(58) Field of Classification Search ............... 128/870, 128/DIG. 23, 202.18, 202.28, 202.29; 602/18, 602/32, 36; 601/41
See application file for complete search history.

(56) References Cited

U.S. PATENT DOCUMENTS

| | | | |
|---|---|---|---|
| 460,451 A | 9/1891 | Shaw | |
| 678,417 A | 7/1901 | Muller | |
| 771,982 A | 10/1904 | Hiser | |
| 1,051,896 A | 2/1913 | Kirkpatrick | |
| 1,397,499 A | 11/1921 | Brennan | |
| 2,528,370 A | 10/1950 | Johnston | |
| 2,851,031 A * | 9/1958 | Ciampa | 602/36 |
| 3,596,655 A * | 8/1971 | Corcoran | 602/32 |
| 3,645,259 A | 2/1972 | Schulman | |
| 4,033,339 A * | 7/1977 | Roberts et al. | 602/18 |
| 4,297,999 A * | 11/1981 | Kitrell | 128/205.16 |
| 4,757,983 A | 7/1988 | Ray et al. | |
| 5,141,489 A * | 8/1992 | Sereboff | 602/18 |
| 5,451,202 A * | 9/1995 | Miller et al. | 602/36 |
| 5,569,175 A * | 10/1996 | Chitwood | 602/32 |

* cited by examiner

*Primary Examiner*—Henry Bennett
*Assistant Examiner*—Camtu Nguyen
(74) *Attorney, Agent, or Firm*—Alex Rhodes

(57) ABSTRACT

A device and method for tilting an unconscious patient's head rearward and lifting his chin to prevent an airway obstruction from developing during intravenous anesthesia when the patient is unconscious but still breathing spontaneously during surgery. The invention is comprised of a neck support for positioning a patient's head in a face-up, supine position and provide a fulcrum for tilting the head rearward on a surface, such as the top surface of an operating table or hospital cart. An extensible swing-arm mounted on an end portion of the neck support carries a cross-arm and a chin support. The swing-arm is rotated, the chin support is engaged with the patient's chin and the patient's head is extended and chin is lifted by an anesthetist provider. The swing-arm and chin cup are mechanically fixed to release the anesthetist provider from the task of maintaining the rearward tilt of the head and chin lifted positions.

11 Claims, 5 Drawing Sheets

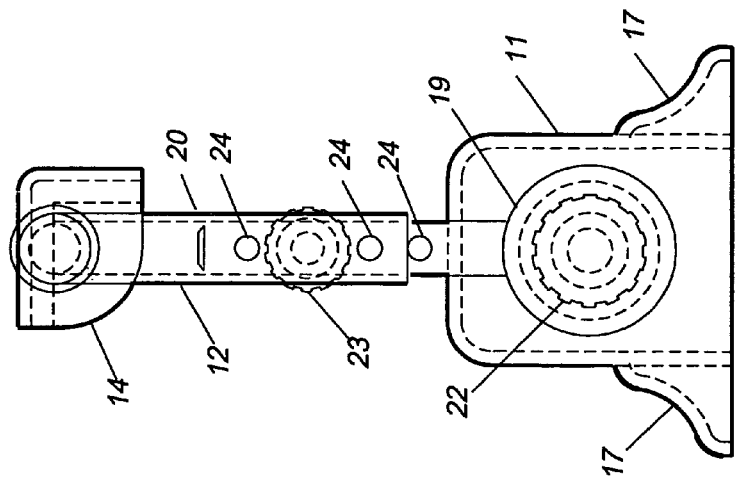
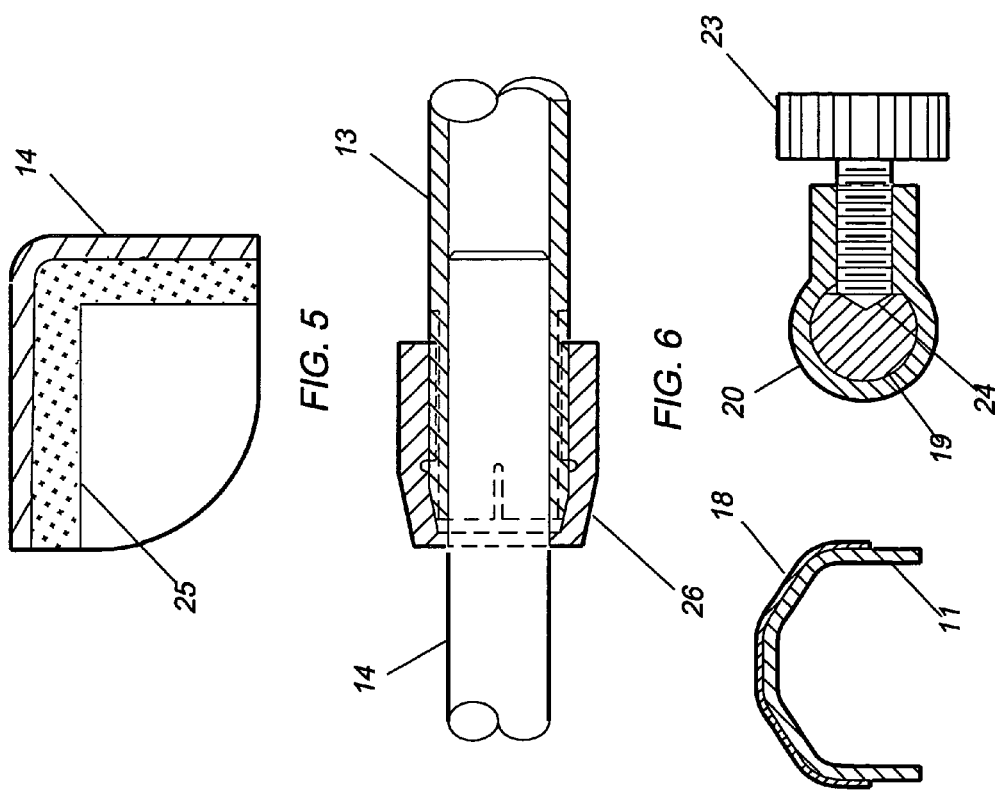

US 7,096,869 B1

DEVICE AND METHOD FOR MAINTAINING AN AIRWAY

FIELD OF THE INVENTION

This invention relates to airway obstructions and more particularly to a device and method for preventing airway obstructions during surgical intraoperative and postoperative procedures.

BACKGROUND OF THE INVENTION

Airway obstructions can strike persons of any age, even children. Risk factors include patients with sleep apnea, being male, overweight, poor health and over the age of forty. They occur in unconscious patients during surgical or postoperative procedures and most commonly occur from sagging tongues and relaxation of upper airway tissues during administration of anesthesia drugs. A lack of immediate intervention allows the patient to obstruct, resulting in hypoxia leading to cardiorespiratory arrest.

The current method of reversing an airway obstruction is for the anesthestist provider to tilt a patient's head backward, lift his chin and thrust the jaw foreward. After the airway has been completely established, the head tilt and chin lift are maintained to prevent the obstruction from re-occurring. This practice is wasteful and prevents the physician from performing other urgent services.

Devices for positioning chins exist in the relevant prior art. U.S. Pat. No. 3,645,259 discloses an inflatable bag for positioning a pilot's chin during an aircraft ejection or a crash. U.S. Pat. Nos. 460,451; 1,051,896; and 2,528,370 disclose chin supports for promoting breathing during sleeping. U.S. Pat. No. 678,417 discloses a chin support for promoting healing of a broken jaw. U.S. Pat. No. 4,757,983 discloses a rest for supporting a patient's head and face in a face-down position. None of these devices is particularly directed to preventing an airway obstruction in an unconscious patient during surgery or postoperative services.

SUMMARY OF THE INVENTION

It is a primary object of the present invention to provide a mechanical device for eliminating the practice of using the anesthestist provider's hands to continuously maintain an airway during surgical and postoperative conditions. With this in mind, the present invention provides an efficient, easy to use device and method lifting a chin and tilting a head without the assistance of the anesthestist provider. An important benefit is that it allows the physician to attend to other urgent matters, such as, monitoring a patient's vital signs, administering intravenous medications and charting.

The invention is comprised of a table top neck support for positioning a patient's head in a face-up position and providing a fulcrum for tilting the head rearward on a surface, such as a face-up position on an operating table or hospital cart; an extensible swing-arm mounted on an end portion of the neck support; a means for selectively positioning the swing-arm about a horizontal axis on the surface of the neck support; a means for selectively adjusting the length of the swing arm; a cross-arm in orthogonal relationship to the swing-arm; a chin support attached to a distal end portion of the cross-arm; and a means for selectively positioning the chin support about a horizontal axis on the cross-arm.

In employing the teaching of the present invention, alternate constructions can be adopted to achieve the desired results and capabilities. Although only one embodiment is discussed, the disclosed embodiment is intended as an example only and should not be considered as limiting the scope of the invention.

Further features and benefits of the invention will be apparent by reference to the drawings and ensuing detailed description of a preferred embodiment which discloses the best mode contemplated in carrying out the invention. The exclusive rights which are claimed are set forth in the numbered claims following the detailed description of the preferred embodiment.

BRIEF DESCRIPTION OF THE DRAWINGS

The invention will be better understood and further objects, characterizing features, details and advantages thereof will appear more clearly with reference to the diagrammatic drawings illustrating preferred features of the invention by way of non-limiting examples only.

FIG. 4 is an end view of the airway clearing device.

FIG. 5 is an enlarged cross-sectional view taken on the line 5—5 in FIG. 3.

FIG. 6 is an enlarged cross-sectional view taken on the line 6—6 in FIG. 3.

FIG. 7 is an enlarged cross-sectional view taken on the line 7—7 in FIG. 3.

FIG. 8 is an enlarged cross-sectional view taken on the line 8—8 in FIG. 3.

DETAILED DESCRIPTION OF A PREFERRED EMBODIMENT

Figure 1:
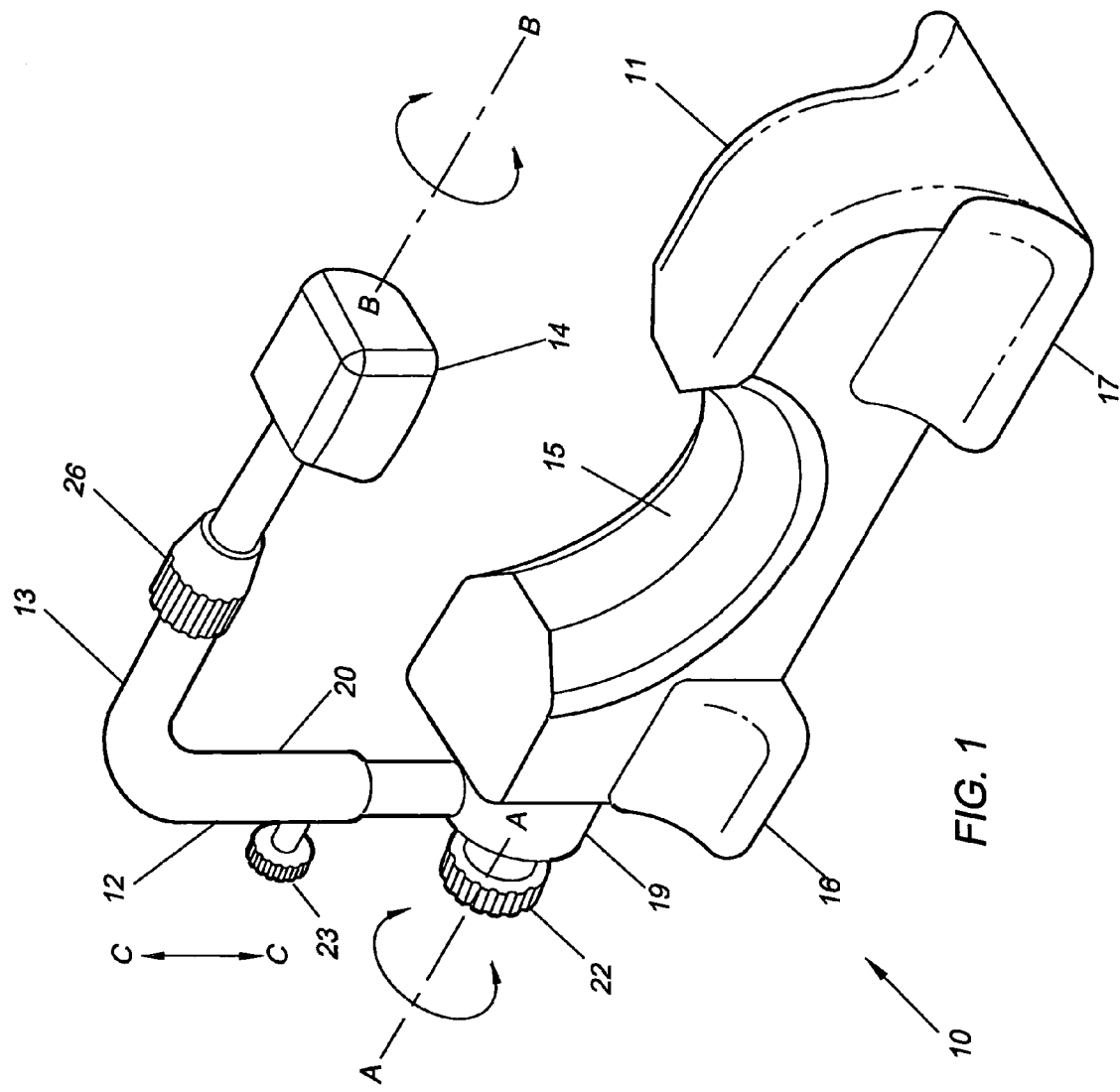
FIG. 1 is a perspective view of a device for treating an unconscious patient's airway obstruction according to the present invention.
Figure 2:
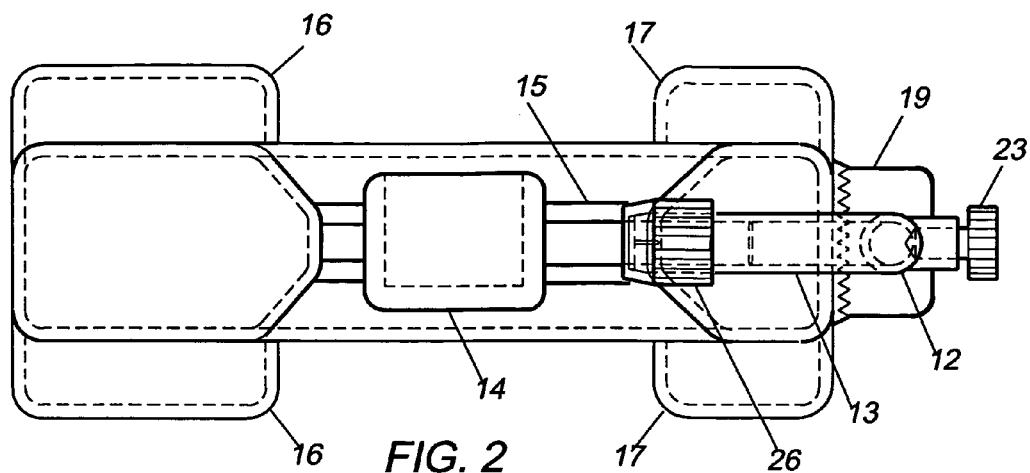
FIG. 2 is a plan view of the airway clearing device.

Referring now to the drawings wherein like numerals designate like and corresponding parts throughout the several views, the device 10 for preventing airway obstructions (herein referred to as an "airway device") is best understood by reference to FIG. 1. It is comprised of a generally rectangular shaped neck support 11; an extensible two-piece swing-arm 12; a cross-arm 13 which is an integral portion of the swing-arm 12 and a chin support 14 attached to a distal end portion of the cross-arm 13. Two styles of construction are contemplated for the airway device 10. The first type is disposable and consists of low molded components made from a plastic, such as polypropylene or polystyrene. The advantage of the disposable style is that it eliminates the requirement of sterilization. The present invention is particularly suitable for a disposable medical appliance because of its moderate cost. The second type is a re-usable type made of metal and/or plastic components which are sterilized and re-used.

The neck support 11 is adapted for a horizontal surface, such as the top surface of an operating table or a hospital cart. It is a thin wall rectangular shaped member with a concave center portion 15 and two pairs of outward extending end portions 16, 17. The concave center portion 15 supports the patient's neck and serves as a fulcrum for tipping the patient's head. The end portions 16, 17 resist tipping. A disposable paper liner 18 preferably covers the concave center portion 15 of the neck support 11.

A lower member 19 of the two-piece swing-arm 12 has a hub shaped portion and an adjoining slender cylindrical portion. An upper member 20 is tubular and telescopically engages the lower member 19. The tubular upper member 20 has a transverse upper portion which serves as the integral cross-arm 13. The lower member 19 of the swing-arm 12 is attached to the neck support 11 with a thumb screw 22. At the juncture of the lower member 19 and 11 neck support are interlocking radial serrations 21 which prevent the swing-arm 12 from rotating when the thumb screw 22 is tightened.

The swing-arm 12 is positioned on the neck support 11 by loosening the thumb screw 22, disengaging the serrations 21, rotating the swing-arm 12 and tightening the thumb screw 22. The telescoping members 19, 20 of the swing-arm are joined together with a pointed thumb screw 23 which threadably engages the tubular swing-arm upper member 20 and bottoms out in conical recesses 24 of the lower member 19.

Figure 3:
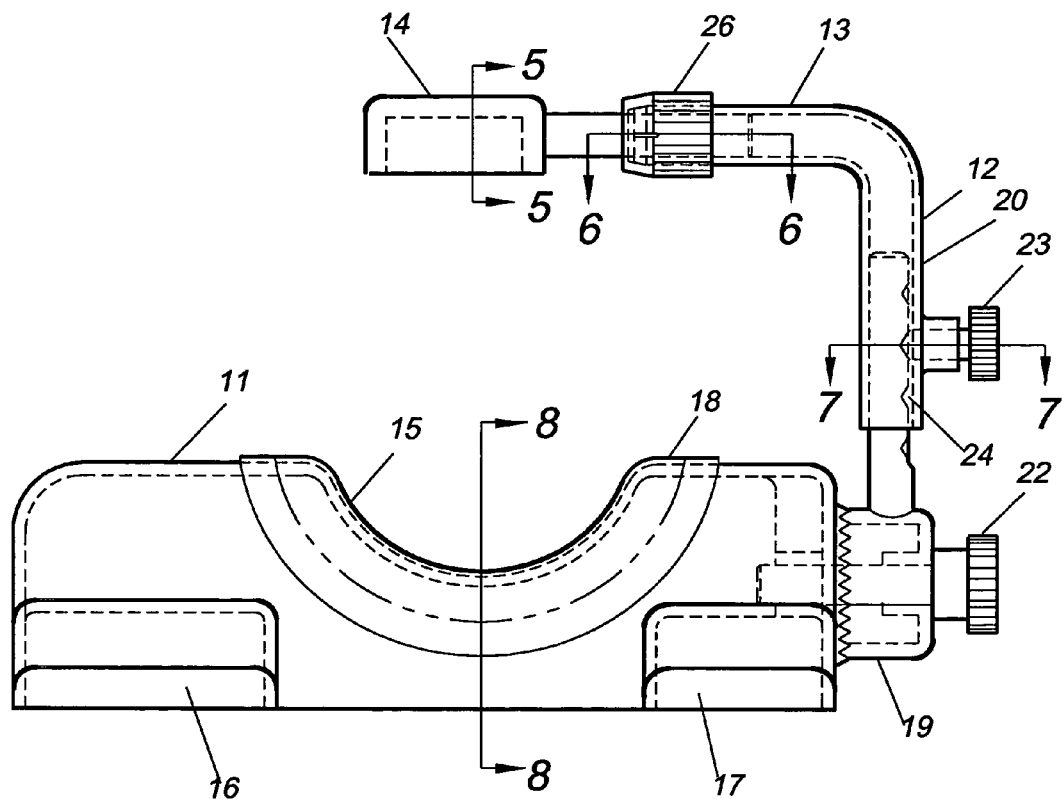
FIG. 3 is a front view of the airway clearing device.

With reference to FIGS. 3 and 5, the chin support 14 is a generally rectangular four sided member with a soft resilient cellular liner 25. The chin support 14 may be disposable or re-usable with a disposable liner.

As shown in FIGS. 3 and 6, the chin support 14 telescopingly engages the cross-arm 13 and is joined to the cross-arm 13 with a hand tightening lock nut 26. The lock-nut 26 prevents the chin support 14 from rotating or axially moving in the cross-arm 13. The distal end portion of the cross-arm 13 is tapered and split to tightly connect the cross-arm 13 with the chin support 14.

Figure 10:
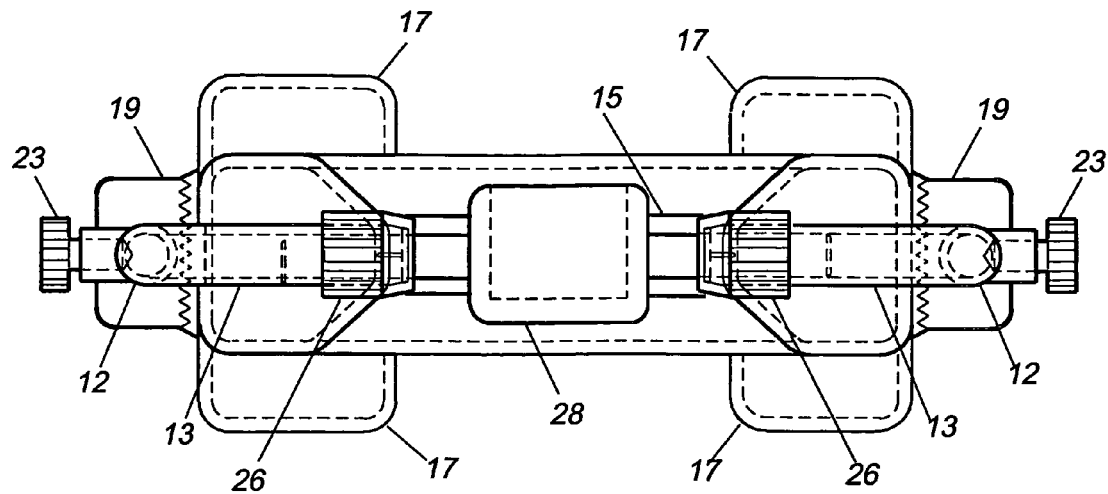
FIG. 10 is a plan view of an alternate embodiment of the airway clearing device.
Figure 11:
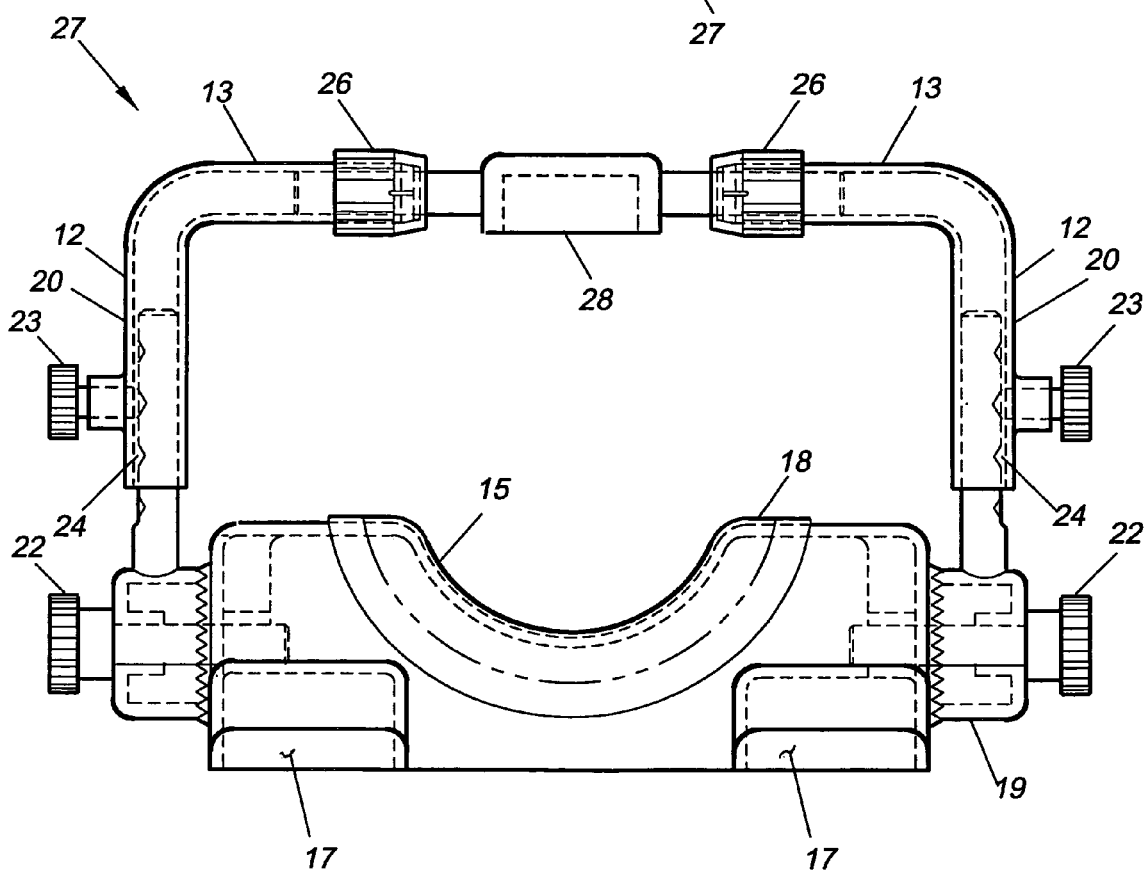
FIG. 11 is a front view of the alternate embodiment of the airway clearing device.

In FIGS. 10 and 11 is shown an alternate embodiment 27 wherein a second swing-arm 12 is provided to straddle mount a chin support 28.

Figure 9:
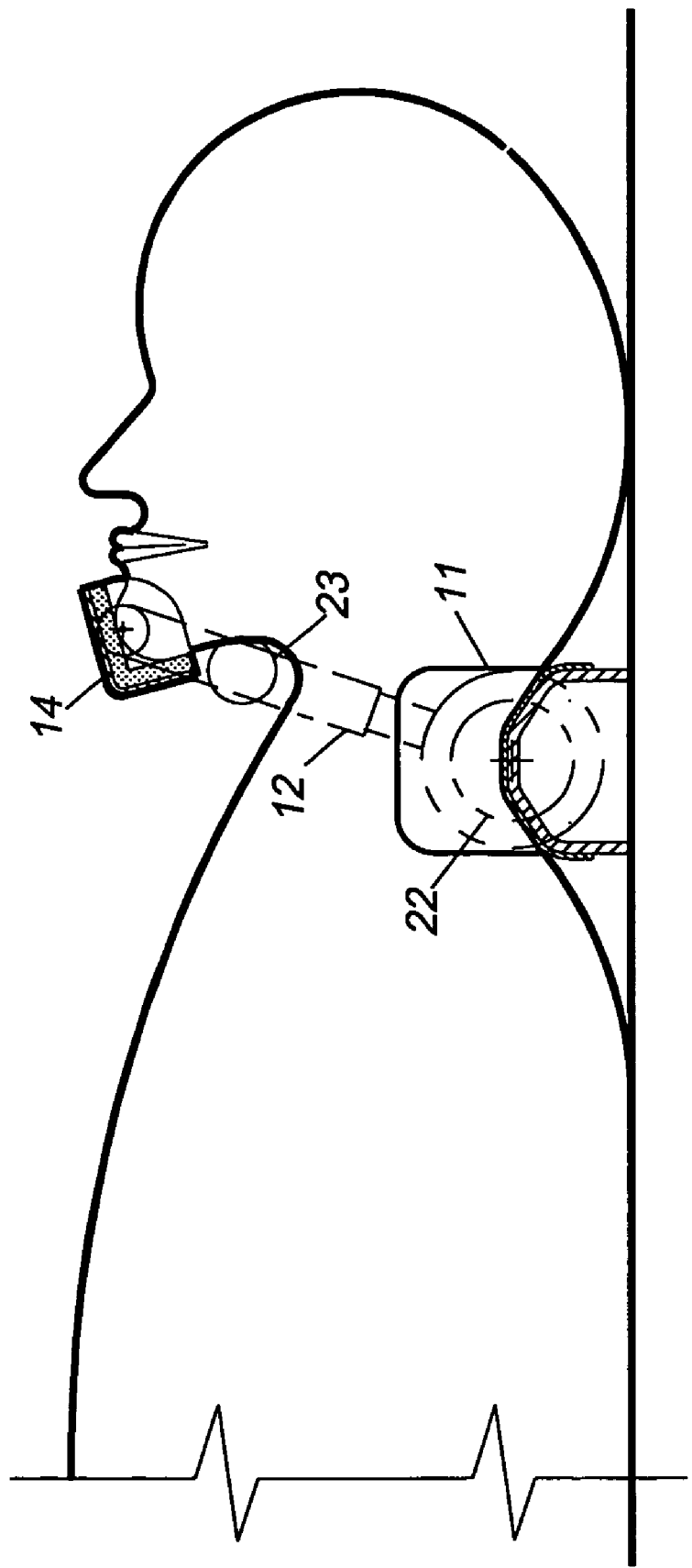
FIG. 9 shows how the airway clearing device is used.

With reference to FIG. 9, the airway device 10 is intended to be used in the following manner. With a patient lying in a face-up position, the airway device 10 is placed under the patient with the patient's neck in the concave portion 15 of neck support 11. The thumb screw 22 which joins the swing-arm 12 to the neck support 11 is loosened to disengage the serrations 21. The swing-arm 12 is rotated about the horizontal axis A—A to position the chin support 14 opposite the patient's chin.

The pointed thumb screw 23 on the cross-arm 13 is loosened and the length of the cross-arm 13 is adjusted in the horizontal direction B—B to align the chin support 14 with the patient's chin. The lock nut 26 is loosened and the chin support 14 is rotated about the horizontal axis C—C and engaged with the patient's chin. The patient's head is tilted rearward and his chin is lifted to establish an open airway avoiding cardiorespiratory arrest. The thumb screws 22, 23 and lock nut 26 are tightened to prevent the obstructed airway from re-occurring. If the patient awakens during the surgical procedure, the lock nut 26 can be disengaged in seconds.

From the above, it is understood that the present invention is an easy to use and effective mechanical device and method for preventing an obstructed airway without the use of an anesthestist provider. Moreover, the device and method allow the physician's hands to be free to perform other urgent services.

Although only a single embodiment has been illustrated and described, it is obvious that other embodiments can be derived after having the benefit of this disclosure by obvious changes to persons skilled in the art, such as substitutions of materials, deletions of parts, re-configurations of parts, additions of parts, re-arrangements of parts, inversions of parts and eliminations of parts without departing from the spirit thereof.

We claim:

1. A device for preventing an airway obstruction in a patient lying on a surface, such as the top surface of an operating table or a hospital cart, by lifting said patient's chin and rotating his head rearwardly and downwardly on an operating table or hospital cart during a surgical or postoperative procedure, said device comprising in combination: a neck engaging support having a concave portion for engaging a rear portion of said patient's neck and elevating said patient's head in a face-up position on a surface, such as the top surface of an operating table or a hospital cart, said neck support acting as a fulcrum to tilt said patient's head rearwardly and downwardly relative to said table or cart; a swing-arm, said swing-arm having an inner end portion attached to an end portion of said neck support for rotation about a horizontal axis; a cross-arm having a first end portion attached to an outer end portion of said swing-arm; and a chin support attached to a second end portion of said cross-arm, said chin support being in lateral aligned relationship with said concave portion of said neck support and selectively adjustable about a second horizontal axis for engaging said patient's chin.

2. The device as recited in claim 1 further comprising a means for selectively adjusting the position of said swing-arm radially about said first horizontal axis.

3. The device as recited in claim 2 wherein said means for selectively adjusting said swing-arm about said first horizontal axis comprises a thumb screw for attaching said swing-arm to said neck support and opposing serrated portions of said swing-arm and said neck support, said opposing serrated portions being in interlocking relationship when said thumb screw is tightened and non-interlocking relationship when said thumb screw is loosened.

4. The device as recited in claim 1 further comprising a means for rotatable adjusting said chin support about said second horizontal axis.

5. The device as recited in claim 4 wherein said chin support telescopically engages said second end portion of said cross-arm and said means for selectively adjusting said chin support about said second horizontal axis comprises a thumb nut for threadably engaging said cross-arm.

6. The device as recited in claim 1 wherein said swing-arm is extensible.

7. The device as recited in claim 1 further comprising a means for extending the distance between said first and said second end portions of said swing-arm.

8. The device as recited in claim 7 wherein said swing-arm is a two-piece arm and said means for extending said distance between said first and said second end portions comprises a pointed thumb screw threadably engaging one of said pieces and a plurality of conical recesses in the other of said pieces for receiving a pointed end portion of said set screw.

9. The device as recited in claim 1 wherein said cross-arm is integral with said neck support.

10. A device for lifting a patient's chin and rotating his head to prevent an airway from being obstructed when said patient is lying face-up on an operating table during a surgical procedure or on a hospital cart during a postoperative procedure, said device comprising in combination: a neck support having a concave portion for elevating said patient's head, supporting said patient's neck on said operating table or said hospital cart, engaging a rear portion of said patient's neck and acting as a fulcrum to tilt said patient's head; a chin support operatively connected to said neck support for lifting said chin and tilting said head rearwardly and downwardly, said chin support being selectively adjustable laterally and rotatable with respect to said neck support to engage said chin support with said patient's chin.

11. A method for lifting a patient's chin and extending his head to prevent an airway obstruction when said patient is lying on an operating table during a surgical procedure or on a hospital cart during a postoperative procedure, comprising the steps of positioning a patient's neck on a neck support which elevates said patient's head and acts as a fulcrum for rotating said patient's head rearwardly and downwardly; rotating a swing-arm about a first horizontal axis to position a chin support under said patient's chin; rotating said chin support about a second horizontal axis to engage said chin support with said patient's chin; lifting said patient's chin and tilting said patient's head with said chin support; and fixing the position of said chin support to maintain said lift of said chin and said tilt of said head and prevent an airway obstruction.

* * * * *